(12) United States Patent
Zheng

(10) Patent No.: US 8,967,194 B2
(45) Date of Patent: Mar. 3, 2015

(54) BYPASS VALVE

(71) Applicant: Beijing Aeonmed Co., Ltd., Beijing (CN)

(72) Inventor: Dianhui Zheng, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 0 days.

(21) Appl. No.: 14/000,865

(22) PCT Filed: Dec. 25, 2012

(86) PCT No.: PCT/CN2012/087372
§ 371 (c)(1),
(2) Date: Oct. 9, 2013

(87) PCT Pub. No.: WO2013/097688
PCT Pub. Date: Jul. 4, 2013

(65) Prior Publication Data
US 2014/0053929 A1 Feb. 27, 2014

(30) Foreign Application Priority Data
Dec. 30, 2011 (CN) .......................... 2011 1 0455688

(51) Int. Cl.
*F16K 15/00* (2006.01)
*A61M 16/20* (2006.01)
(Continued)

(52) U.S. Cl.
CPC ............. *A61M 16/20* (2013.01); *A61M 16/183* (2013.01); *F16K 15/148* (2013.01); *A61M 16/208* (2013.01)
USPC .................... 137/516.11; 137/614.2; 137/854

(58) Field of Classification Search
USPC ............ 137/493, 493.9, 599.11, 599.03, 602, 137/605, 614.2, 516.11, 516.13, 516.17, 137/516.19, 516.21, 854; 128/205.24, 128/203.13
See application file for complete search history.

(56) References Cited

U.S. PATENT DOCUMENTS 2,841,142 A * 7/1958 Hay .......................... 128/205.13
3,630,197 A * 12/1971 Hirano ...................... 128/204.26
(Continued)

FOREIGN PATENT DOCUMENTS

CN 101584897 A 11/2009
CN 101943279 A 1/2011
(Continued)

OTHER PUBLICATIONS

International Search Report issued in International Application No. PCT/CN2012/087372 dated Apr. 4, 2013.

*Primary Examiner* — Craig Schneider
*Assistant Examiner* — Jessica Cahill
(74) *Attorney, Agent, or Firm* — Venable LLP; Robert Kinberg; F. Brock Riggs

(57) ABSTRACT

Disclosed is a bypass valve comprising a valve body. The valve body has a gas inlet and a gas outlet, wherein a check valve is provided at the air outlet. The check valve comprises a check valve body, a ventilation plate and a first sealing gasket. A first gas passage for gas delivering is provided within the check valve body; ventilation holes are provided on the ventilation plate; the ventilation holes are in communication with the gas outlet; the first sealing gasket is provided between the ventilation plate and the check valve body; and the first gas passage and the ventilation holes are in selective communication with each other via the first sealing gasket. The uni-directional check valve is provided in the gas air outlet in the bypass valve, causing the direction of the gas flow to be unique, overcoming the problem of imprecise concentration of the anaesthetic gas caused by the a gas backflow, and having the advantage of structural technology and better gas tightness.

8 Claims, 6 Drawing Sheets

(51) Int. Cl.
*A61M 16/18* (2006.01)
*F16K 15/14* (2006.01)

(56) References Cited

U.S. PATENT DOCUMENTS

| | | | |
|---|---|---|---|
| 3,795,257 A | | 3/1974 | Fabish et al. |
| 3,933,171 A | * | 1/1976 | Hay ................ 137/493.7 |
| 4,121,580 A | * | 10/1978 | Fabish ............. 128/205.11 |
| 4,274,404 A | * | 6/1981 | Molzan et al. ...... 128/204.25 |
| 5,002,050 A | * | 3/1991 | McGinnis ......... 128/204.18 |
| 5,239,990 A | * | 8/1993 | Delphia ........... 128/201.11 |
| 5,381,836 A | * | 1/1995 | Braatz et al. ........... 141/21 |
| 7,341,059 B2 | * | 3/2008 | Moody et al. ...... 128/205.24 |
| 2010/0163030 A1 | * | 7/2010 | Hyman et al. ..... 128/203.12 |
| 2010/0319690 A1 | * | 12/2010 | Cuzydlo ........... 128/203.12 |

FOREIGN PATENT DOCUMENTS

| | | |
|---|---|---|
| CN | 102109052 A | 6/2011 |
| CN | 202397935 U | 8/2012 |
| CN | 202590121 U | 12/2012 |
| GB | 750152 A | 6/1956 |

* cited by examiner

BYPASS VALVE

TECHNICAL FIELD

The present invention relates to the field of medical instruments, in particular to a bypass valve.

TECHNICAL BACKGROUND

An anesthesia machine, which is an equipment very demanding for security, stability and operability used in the operating room, is applicable to deliver an anesthetic into pulmonary alveoli of a patient via a mechanical circuit and form a partial pressure of anesthetic gas in the pulmonary alveoli. The anesthetic has a direct inhibition action on the central nervous system after being diffused into blood, resulting in an effect of general anesthesia. The anesthesia machine preliminarily includes four parts of a gas supply system, a vaporizer, a ventilator and a circuit system.

The anesthetic evaporator, as a vital component in the anesthesia machine, is introduced to the anesthesia machine to provide the patient with a stable anesthetic gas mixture of an accurate concentration. The anesthetic evaporator can effectively evaporate the anesthetic, and also accurately control the concentration of the outputted anesthetic vapor.

The anesthetic evaporator is incorporated into the anesthesia machine through a bypass valve. When the anesthetic evaporator is not connected, the anesthesia machine delivers gas to the patient via the bypass valve, in this case, the bypass valve functions as a passage for transmitting the gas, and therefore should be leakage-proof to prevent the leakage of the gas. Poor gas tightness of the bypass valve may cause the leakage of a part of the gas, thus resulting in a waste of resources. Meanwhile, it should be ensured that the gas flowing through the bypass valve does not encounter gas resistance or encounters little gas resistance, thus providing smoothly the patient with the gas. When the anesthetic evaporator is connected, a gas passage within the bypass valve is closed, all the gas flows through the anesthetic evaporator, enters again into the anesthesia machine via the bypass valve after being outputted by the evaporator, and then is delivered to the patient. In this case, the bypass valve should be leakage-proof to prevent the leakage of the anesthetic. Poor gas tightness of the bypass valve may cause the leakage of the anesthetic, causing not only a waste of resources, but also an anesthesia to doctors, which has a great impact on the surgery quality and patient safety.

Traditional bypass valve includes a gas inlet and a gas outlet. In use, the gas from the gas inlet enters into the evaporator via the bypass valve, flows to the downstream of the anesthesia machine through the gas outlet of the bypass valve after being outputted by the evaporator, and then is delivered to the patient. In practice, a gas backflow occurs to the bypass valve in the case of pressure fluctuation at the gas outlet, resulting in a concentration of the outputted anesthetic gas that is not precise enough to be used conveniently; meanwhile, the traditional bypass valve has still defects such as a structural and technological defect, poor gas tightness, and so on.

SUMMARY OF THE INVENTION

An object of the present invention is to solve the problem of a gas backflow phenomenon caused by the pressure fluctuation at the gas outlet of the traditional bypass valve, which further causes the imprecise concentration of the outputted anesthetic gas. Therefore, the present invention provides a bypass valve, in which a check valve is introduced at the gas outlet of the bypass valve, to allow the gas to flow unidirectionally without causing the gas backflow phenomenon, and the inventive bypass valve has advantages of a good structure and good gas tightness.

The object of the present invention is achieved by the technical solution below.

A bypass valve includes a valve body, which includes a gas inlet and a gas outlet. a check valve including a check valve body, a ventilation plate and a first sealing gasket is arranged at the gas outlet, a first gas passage for gas delivering is arranged within the check valve body, the ventilation plate contains a ventilation hole in communication with the gas outlet, the first sealing gasket is arranged between the ventilation plate and the check valve body, and the first gas passage is selectively communicated with the ventilation hole by the first sealing gasket.

Further, a valve cover containing a second gas passage is arranged on the valve body of the bypass valve, the valve body of the bypass valve contains a third gas passage, a first cavity in communication with the gas inlet and a second cavity in communication with the first cavity, and the second cavity and the third gas passage are used for gas delivering when the bypass valve is not communicated with an evaporator.

Preferably, stepwise annular grooves comprising a first annular groove and a second annular groove are arranged on the valve body of the bypass valve at the gas outlet, the ventilation plate is arranged in the first annular groove, the check valve body is arranged adjacent to the outer side face of the ventilation plate and fixed to the valve body of the bypass valve by a screw, a sealing ring is arranged in the connection joint between the ventilation plate and the valve body of the bypass valve, and a sealing ring is arranged in the connection joint between the check valve body and the valve body of the bypass valve.

Preferably, inner threads are arranged in an upper part of the first cavity, and the valve cover is provided with external threads matching with the inner threads, such that the valve cover is threadedly connected to the valve body; two grooves are circumferentially arranged on the valve cover at an upper side and a lower side of the external threads respectively and each are used for accommodating the sealing rings; the sealing ring located at the upper side of the external threads is used for enhancing the gas tightness between the valve cover and the evaporator, while the other one located at the lower side of the external threads is used for enhancing the gas tightness between the valve cover and the valve body of the bypass valve;

the third gas passage is arranged under the first cavity and connected with the bottom of the first cavity, such that the second gas passage and the third gas passage are opposite to each other; a first boss corresponding to the outlet of the second gas passage is arranged at the bottom of the valve cover, and a second boss corresponding to the inlet of the third gas passage is arranged at the bottom of the first cavity.

Further, a third annular groove in communication with the first gas passage is arranged at an end of the check valve body that is connected with the ventilation plate;

the ventilation plate is substantially circular, a stepwise surface for mounting the sealing ring is arranged around the periphery of the ventilation plate, and the ventilation plate contains a center hole and a plurality of ventilation hole;

the first sealing gasket is arranged between the ventilation plate and the check valve body, and the gas outlet and the first gas passage are selectively communicated with each other by a movement of the first sealing gasket.

Further, a valve core is arranged in an assembly space formed by the second gas passage, the first cavity and the third gas passage, a second sealing gasket is arranged on the valve core and located between the first boss and the second boss, and the first cavity is selectively communicated with the second gas passage or the third gas passage by an up-and-down movement of the second sealing gasket.

Further, the first sealing gasket includes a disc and a rod arranged at the center of the disc, the first sealing gasket is arranged between the ventilation plate and the check valve body, the rod is extended through the center hole, the length of the rod is greater than the thickness of the ventilation plate, and a limit cap is arranged at a free end of the rod to prevent the first sealing gasket from releasing from the ventilation plate; when the disc is attached to the ventilation plate, the communication between the ventilation hole and the third annular groove is blocked, and hence the communication between the gas outlet and the first gas passage is blocked.

Further, the valve core includes a gland, an upper spring, a valve stem and a lower spring, which are sequentially connected from top to bottom;

a first projection is arranged at the upper portion of the gland, a second projection corresponding to the first projection is inwardly arranged at the top of the valve cover and located at an inlet of the second gas passage, the gland is limited within the second gas passage by the engagement between the first projection and the second projection, the gland is substantially cylindrical, four flat faces are formed evenly and longitudinally at the periphery of the gland, and guide portions with an arc-shaped cross section are arranged between the flat faces.

Further, the outer diameter of the disc is smaller than the inner diameter of the third annular groove, a plurality of limit projections are arranged within the third annular groove, which is in communication with the first gas passage, and a pipe joint for exhausting gas is threadedly connected to the outer end of the first gas passage.

Further, an upper installation groove is extended upwardly and inwardly from the bottom of the gland at the center of the gland and is chamfered at its opening, a lower installation groove is extended downwardly and inwardly from the top of the valve stem at the center of the valve stem, one end of the upper spring is arranged in the upper installation groove, while the other end of the upper spring is arranged in the lower installation groove;

an annular body is arranged in the middle of the valve stem, the upper surface of the annular body is tapered, an installation groove for the second sealing gasket is arranged on the valve stem immediately following the lower surface of the annular body, the second sealing gasket is arranged on the valve stem through the installation groove for the second sealing gasket, and a lower part of the valve stem extends through the lower spring, one end of which is arranged in the third gas passage and the other end of which is contacted with the lower surface of the second sealing gasket.

The beneficial effects of the present invention are described below. A check valve is arranged at the gas outlet of the valve body, and the check valve is opened when the gas flows in a normal direction and then smoothly flows out; when a pressure fluctuation at the gas outlet results in a gas reverse backflow, the check valve is closed to prevent the gas backflow, such that the concentration of the outputted anesthetic gas is accurate, reliable, and consistent with a preset value. Specifically, the check valve includes a check valve body and a ventilation plate, both of which achieve the open or close of the check valve by coordinating with the first sealing gasket. When the gas flows in the normal direction, i.e. from the first cavity to the gas outlet, the sealing gasket is pushed to move towards the first gas passage under the action of the gas pressure, such that a gap is present between the first sealing gasket and the ventilation plate, and the gas flows from ventilation holes towards the first gas passage, and then is outputted; and when the gas flows in a reverse direction, i.e. the gas flows inwardly from the first gas passage, the first sealing gasket is attached to the ventilation plate under the action of the gas pressure, such that the communication between the first gas passage and the gas outlet is blocked, and the gas cannot flow into the bypass valve from the first gas passage. With two sealing rings arranged at the connection joint between the valve cover and the valve body, the gas tightness between the valve cover and the valve body or an evaporator is enhanced. Sealing rings are arranged at the connection joints between the valve body and the check valve body as well as the ventilation plate, which enhances the gas tightness between the check valve and the valve body. Compared to prior art, the inventive bypass valve has advantages of ensuring a unidirectional gas flow, a simple structure and better gas tightness.

DESCRIPTION OF DRAWINGS

The present invention will be further described in detail by way of the embodiment below in conjunction with the accompanying drawings.

A LIST OF THE REFERENCE NUMERALS

1: Valve body; 11: First cavity; 12: Second cavity;
13: Third gas passage; 14: First annular groove; 15: Second annular groove;
16: Second boss; 17: First groove;
2: Valve cover; 21: Second gas passage; 22: Second projection;
23: First boss; 24: Second groove; 25: Third groove;
3: Valve core; 31: Gland; 311: First projection;
312: Upper installation groove; 313: Guide portion;
32: Upper spring;
33: Valve stem; 331: Lower installation groove;
332: Annular body; 333: Installation groove for the second sealing gasket;

34: Lower spring; 35: Second sealing gasket;
4: Check valve; 41: Check valve body; 411: First gas passage;
412: Third annular groove; 413: Limit projection; 42: Ventilation plate;
421: Ventilation hole; 422: Stepwise surface;
43: First sealing gasket; 431: Disc; 432: Rod;
433: Limit cap;
5: Sealing ring;
6: Pipe joint.

DETAILED DESCRIPTION OF THE PREFERRED EMBODIMENT

Figure 1:
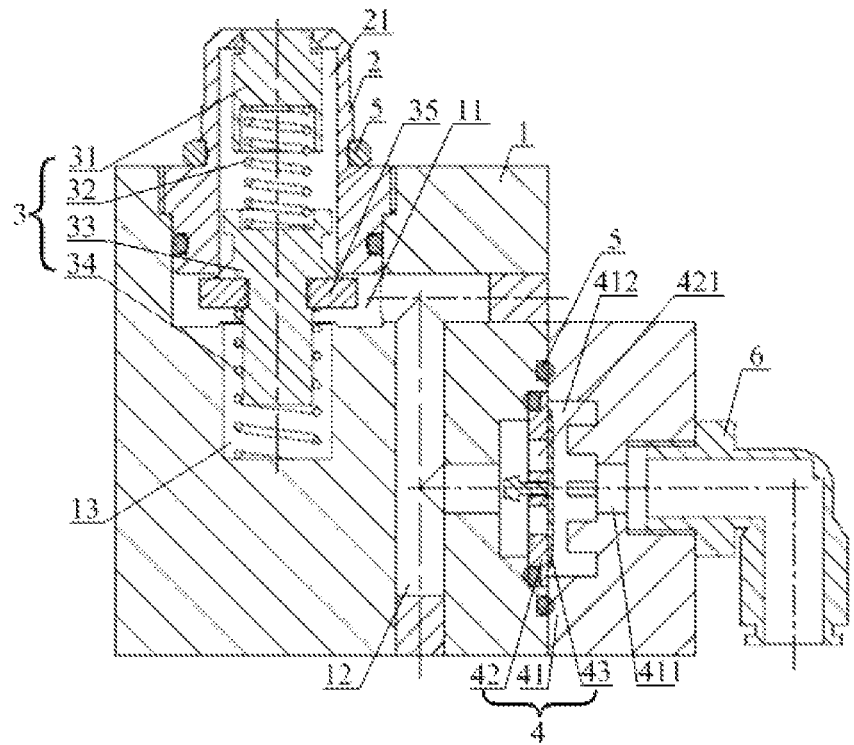
FIG. 1 is a schematic partial sectional view of a bypass valve according to the present invention.

As shown in FIG. 1, in an embodiment, a bypass valve according to the present invention includes a valve body 1, which includes a gas inlet 18 and a gas outlet. A check valve 4 including a check valve body 41, a ventilation plate 42 and a first sealing gasket 43 is arranged at the gas outlet. A first gas passage 411 for transmitting the gas is arranged within the check valve body 41, the ventilation plate 42 is provided with ventilation holes 421 in communication with the gas outlet, and the first sealing gasket 43 is arranged between the ventilation plate 42 and the check valve body 41, so that the first gas passage 411 is selectively communicated with the ventilation holes 421 by the first sealing gasket 43. When the gas flows out from the gas outlet, the check valve 4 is opened in that a gap is present between the first sealing gasket 43 and the ventilation plate 42, such that the ventilation holes 421 are in communication with the first gas passage 411, and hence the gas can be outputted normally. When the pressure fluctuation at the gas outlet results in a gas backflow, the check valve 4 is closed in that the first sealing gasket 43 rests tightly on the ventilation plate 42 to block the communication between the ventilation holes 421 and the first gas passage 411, and hence the gas cannot flow back into the bypass valve.

A valve cover 2 is provided on the valve body 1. A valve core 3, which includes a gland 31, an upper spring 32, a valve stem 33 and a lower spring 34 connected in sequence from top to bottom, is arranged between the valve cover 2 and the valve body 1, and a second sealing gasket 35 is arranged around the valve core 3.

Figure 2:
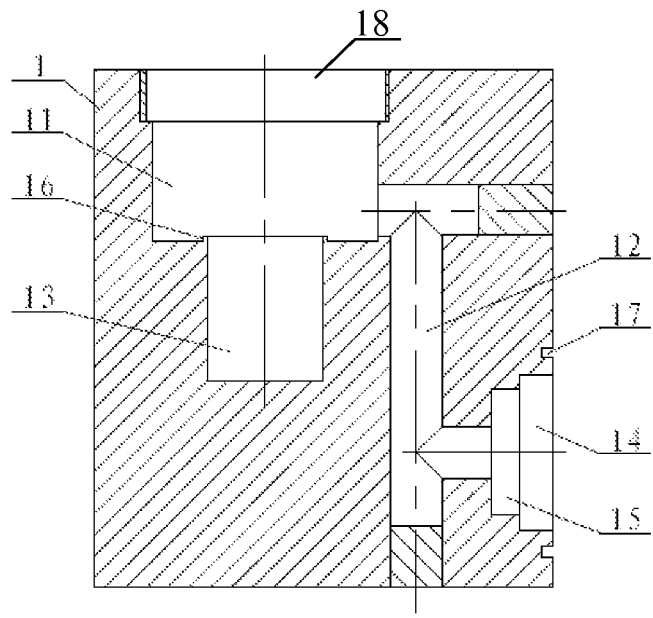
FIG. 2 is a schematic sectional view of a valve body shown in FIG. 1.

FIG. 2 shows a specific embodiment of the valve body. The valve body 1 includes a first cavity 11 in communication with the gas inlet (not shown), a second cavity 12 in communication with the first cavity 11, and a third gas passage 13. The upper part of the first cavity 11 is provided with inner threads for threadedly connecting with the valve cover 2. The second cavity 12 and the third gas passage 13 are used for transmitting the gas when the bypass valve is not in communication with an evaporator. The third gas passage 13 is arranged under the first cavity 11 and in communication with the bottom of the first cavity 11. A second boss 16 corresponding to the inlet of the third gas passage 13 is arranged at the bottom of the first cavity 11. Two concentric annular grooves, i.e. a first annular groove 14 and a second annular groove 15, and a first groove 17 are arranged at the gas outlet. The first annular groove 14 is used for accommodating the ventilation plate 42 of the check valve, and the first groove 17 is used for receiving a sealing ring 5. Since the sealing ring 5 is located in the connection joint between the check valve and the bypass valve, the sealing ring 5 can enhance the gas tightness between the check valve and the bypass valve.

Figure 3:
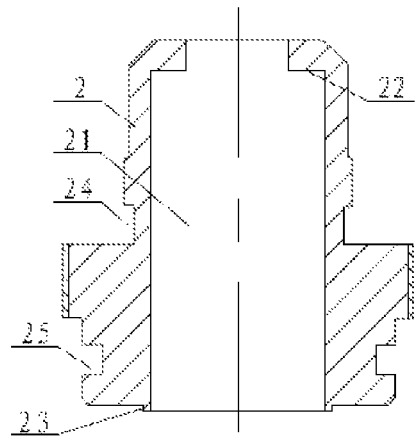
FIG. 3 is a schematic sectional view of the valve cover shown in FIG. 1.
Figure 4:
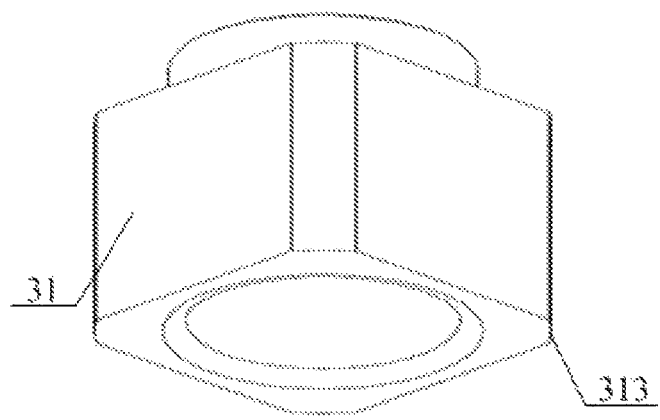
FIG. 4 is a schematic perspective view of a gland shown in FIG. 1.
Figure 5:
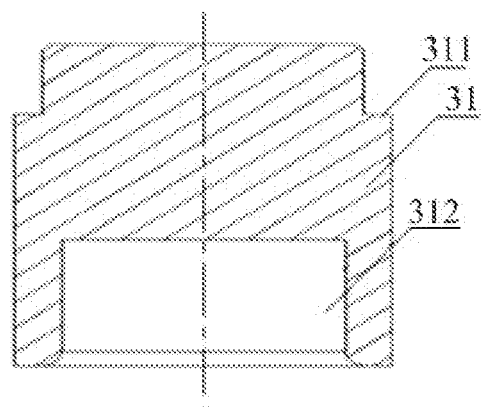
FIG. 5 is a schematic sectional view of the gland shown in FIG. 1.
Figure 6:
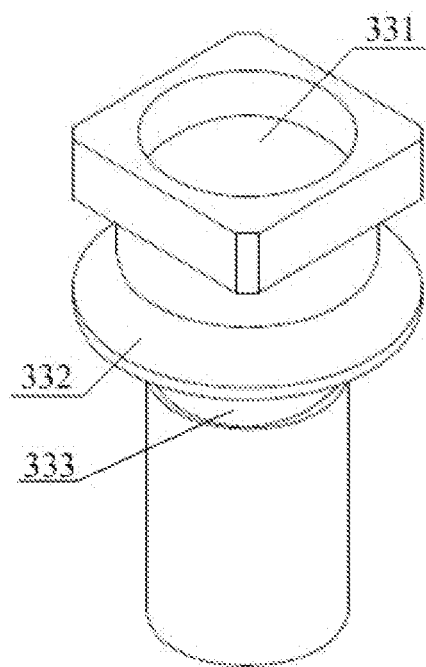
FIG. 6 is a schematic perspective diagram of a valve stem shown in FIG. 1.
Figure 7:
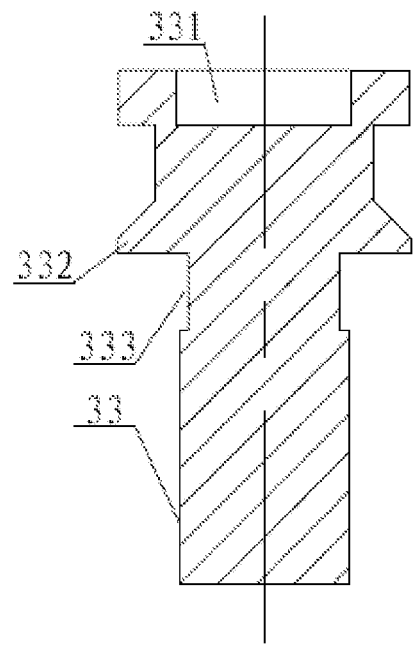
FIG. 7 is a schematic sectional view of the valve stem shown in FIG. 1.
Figure 8:
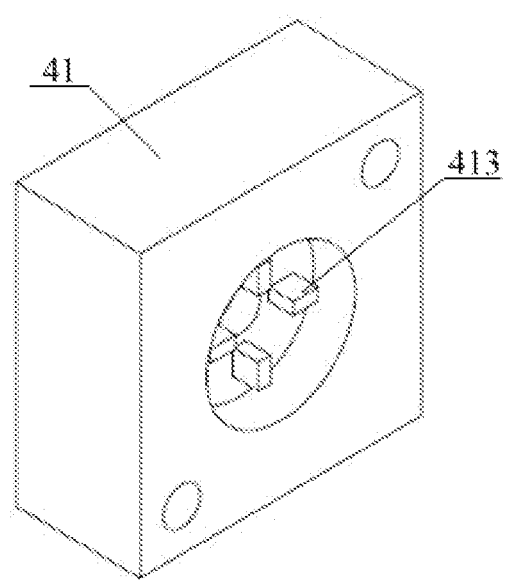
FIG. 8 is a schematic perspective view of a check valve body shown in FIG. 1.
Figure 9:
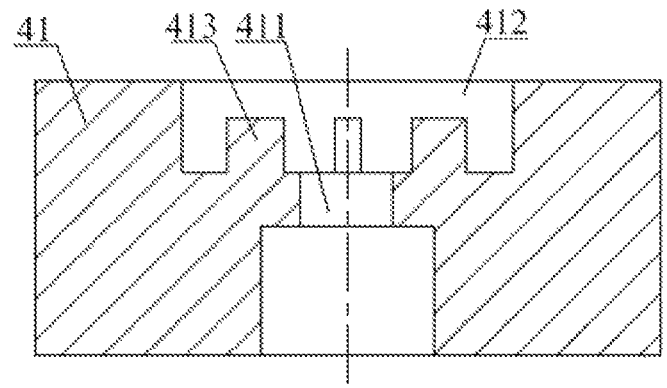
FIG. 9 is a schematic sectional view of the check valve body shown in FIG. 1.
Figure 10:
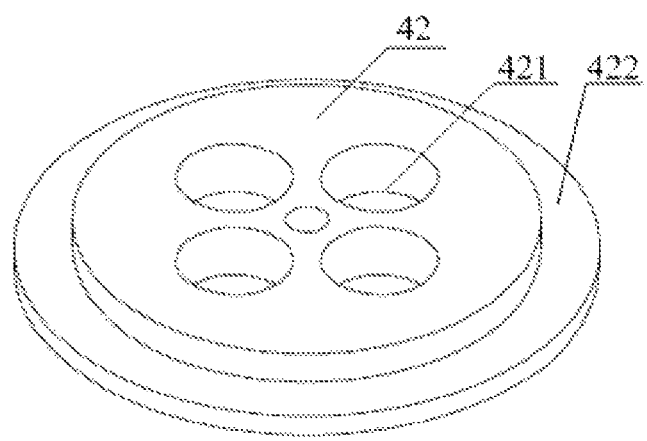
FIG. 10 is a schematic perspective view of a ventilation plate shown in FIG. 1.
Figure 11:
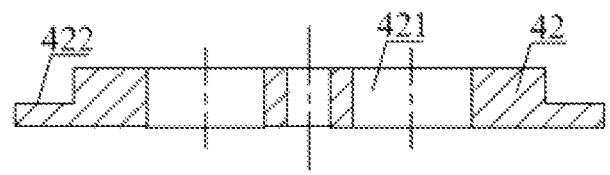
FIG. 11 is a schematic sectional view of the ventilation plate shown in FIG. 1.
Figure 12:
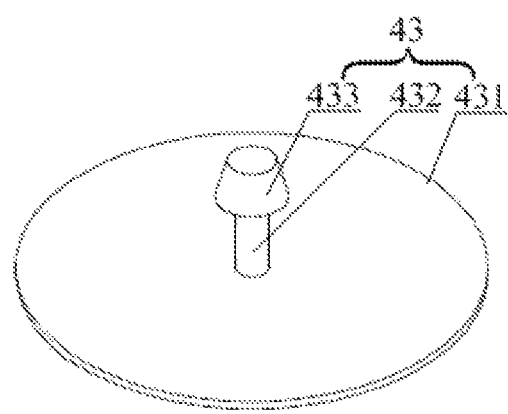
FIG. 12 is a schematic perspective view of a first sealing gasket shown in FIG. 1.

FIG. 3 shows a specific embodiment of the valve cover. The valve cover 2 has a hollow structure with an internal second gas passage 21, an outlet of which is at the bottom of the valve cover and an inlet of which is at the top of the valve cover, and the anesthetic gas enters from the inlet and is exhausted from the outlet. A first boss 23 corresponding to the outlet of the second gas passage 21 is arranged at the bottom of the valve cover 2, a second projection 22 is inwardly arranged at the top of the valve cover 2, and external threads are arranged on the intermediate part of the valve cover 2. A second groove 24 and a third groove 25 are arranged on the valve cover 2 on the upper side and the lower side of the external threads, respectively, and a sealing ring 5 is arranged in each of the second and third grooves. When the valve cover 2 is threadedly assembled on the valve body 1, the sealing ring 5 on the upper side of the threads ensures good gas tightness between the valve cover 2 and a evaporator, while the sealing ring 5 on the lower side of the threads ensures good gas tightness between the valve body 1 and the valve cover 2.

FIGS. 1, and 4-7 show a specific embodiment of the valve core. The valve core 3 includes a gland 31, an upper spring 32, a valve stem 33 and a lower spring 34. The gland 31 is substantially cylindrical, but four flat faces are formed evenly and longitudinally at the periphery of the gland 3, such that gas passages are formed between the valve cover 2 and the gland 3, and guide portions 313 with an arc-shaped cross section are arranged between the flat faces to enable the gland 31 to move sufficiently stably and reliably within the valve cover 2. A lateral first projection 311 is arranged at the upper portion of the gland 31, an upper installation groove 312 is extended upwardly and inwardly from the bottom of the gland 3 at the center of the gland 3 and is chamfered at its opening for the sake of mounting the upper spring. A lower installation groove 331 is extended downwardly and inwardly from the top of the valve stem 33 at the center of the valve stem 33. An annular body 332 is arranged in the middle of the valve stem 33, the upper surface of the annular body 332 is tapered, and an installation groove 333 for the second sealing gasket is arranged on the valve stem 33 immediately following the lower surface of the annular body 332.

For the purpose of assembling, one end of the upper spring 32 is arranged in the upper installation groove 312, and the other end of the upper spring 32 is arranged in the lower installation groove 331. The second sealing gasket 35 is arranged on the valve stem 33 through the installation groove 333 for the second sealing gasket. The lower part of the valve stem 33 extends through the lower spring 34, one end of which is arranged in the third gas passage 13, and the other end of which is contacted with the lower surface of the second sealing gasket 35. The valve core 3 is then aligned with the inner of the valve cover 2, and the valve cover 2 is screwed on the valve body 1 while pressing the upper spring 32 and lower spring 34. The gland 31 is limited in the second gas passage 21 by pressing the first projection 311 tightly on the second projection 22. The second gas passage 21 and the third gas passage 13 are opposite to each other and the second sealing gasket 35 is located between the first boss 23 and the second boss 16, therefore, when the sealing gasket 35 is moved upwardly and pressed tightly on the first boss 23, the second gas passage 21 is blocked and the first cavity 11 is in communication with the third gas passage 13; and when the second sealing gasket 35 is moved downwardly and pressed tightly on the second boss 16, the third gas passage 13 is blocked and the first cavity 11 is in communication with the second gas passage 21.

FIGS. 1 and 8-12 show a specific embodiment of the check valve. The check valve 4 is arranged at the gas outlet and includes the check valve body 41 and the ventilation plate 42. A first gas passage 411 is arranged within the check valve body 41, a third annular groove 412 is arranged at the inlet of the first gas passage 411, a plurality of limit projections 413 are arranged within the third annular groove 412, and a pipe joint 6 is threadedly connected to the outlet of the first gas passage 411. The check valve body 41 is provided with a threaded hole for connecting the check valve body 41 to the valve body 1 by a screw;

The ventilation plate 42 is substantially circular and contains a center hole and four ventilation holes 421. A stepwise surface 422 is arranged around the periphery of the ventilation plate 422, and a sealing ring 5 may be placed on the stepwise surface 422.

The first sealing gasket 43 including a disc 431 and a rod 432 is arranged between the ventilation plate 42 and the check valve body 41. The rod 432 is arranged at the center of the disc 432, and the length of the rod 432 is greater than the thickness of the ventilation plate 42, such that the rod 42 can be moved back and forth in the center hole of the disc 432. For the purpose of avoiding the first sealing gasket 43 to release from the ventilation plate 42, a limit cap 333 is arranged at a free end of the rod 432. The dimension of the limit cap 433 is greater than the diameter of the center hole, and a plurality of limit projection 413 are arranged in the third annular groove 412 to limit the position of the disc 431.

For the purpose of assembling, both the rod 432 and the limit cap 433 are passed through the centre hole of the ventilation plate 42, both the ventilation plate 42 and the sealing ring 5 are arranged in the first annular groove 14 such that the limit cap 433 is located in the second annular groove 15, and then the disc 431 is adhered to the rod 432. The sealing ring 5 is arranged in the first annular groove 17, the disc 431 is aligned with the third annular groove 412, and the check valve 41 is tightly fixed to the valve body 1 by a screw. The outer diameter of the disc 431 is smaller than the inner diameter of the third annular groove 412, and the disc 431 is arranged in the third annular groove 412, therefore, the disc 431 can block the ventilation holes 421 when being attached tightly to the ventilation plate 42, such that the gas outlet is not in communication with the first gas passage 411.

The operating principle of the bypass valve according to the present invention is described below. As shown in FIG. 1 which presents a partial structure of the bypass valve according to the present invention, the bypass valve includes actually two identical valve covers, which are arranged on the valve body, and the valve body contains two independent gas passages. When the evaporator is not connected, the bypass valve actually functions as a gas passage, the gas flows from an intake pipe joint into the valve body and is finally outputted from the second cavity 12. When the evaporator is connected, those two valve covers cooperate with the evaporator (i.e., the same evaporator is required to cooperate with both of the two valve covers for the purpose of connecting with the bypass valve), the gas flows into the valve body from the intake pipe joint, into the evaporator from the first valve cover, then into the valve body again from the evaporator through the second valve cover, and finally is outputted from the pipe joint at the gas outlet. The upper portion of the valve cover is designed with a hexagonal structure, to facilitate the assembly between the valve cover and the valve body, (i.e., the peripheral structure of the valve cover is mainly used for matching with an assemble tool), and each bypass valve can be connected to one or more evaporators at the same time.

When the evaporator is not connected, the bypass valve actually functions as a gas passage, and the second cavity 12 is the gas outlet portion of the gas passage. In this case, the gland 31 is not pressed down, and the second sealing ring 35 is pressed tightly on the first boss 23 under the action of the elastic force of the lower spring 34, thus the second gas passage 21 is blocked, the gas enters into the third gas passage 13 from the gas inlet, into the second cavity 12 through the first cavity 11, and then arrives at the downstream of the anesthesia machine through pipes and joints (not shown) of the bypass valve.

When the evaporator is connected, the gland 31 is pressed down, such that the second sealing gasket 35 is moved downwards and pressed tightly on the second boss 16 against the elastic force of the lower spring 34, thus the third gas passage 13 is blocked, and the anesthetic gas enters into the first cavity 11 from the second gas passage 21 and flows to the gas outlet through the second cavity 12. When the gas enters into the second annular groove 15, the first sealing gasket 43 is pushed to the right by the gas pressure, such that a gap is present between the first sealing gasket 43 and the ventilation plate 42, and the gas flows into the third annular groove 412 from the ventilation holes 421 through the gap, then into the first gas passage 411, and finally is outputted from the pipe joint 6.

In case the gas enters into the first gas passage 411 from the pipe joint 6 and the gas backflow is caused, the gas pressure pushes the first sealing gasket 43 to move to the left, and the disc 431 is attached tightly to the ventilation plate 42 and blocks the ventilation holes 421, such that the first gas passage 411 is not in communication with the gas outlet and the gas cannot flow back into the valve body 1.

The invention claimed is:

1. A bypass valve, comprising a valve body with a gas inlet and a gas outlet, wherein, a check valve including a check valve body, a ventilation plate and a first sealing gasket is arranged at the gas outlet, a first gas passage for gas delivering is arranged within the check valve body, the ventilation plate contains a ventilation hole in communication with the gas outlet, the first sealing gasket is arranged between the ventilation plate and the check valve body, and the first gas passage is selectively communicated with the ventilation hole by the first sealing gasket, wherein, stepwise annular grooves comprising a first annular groove and a second annular groove are arranged on the valve body of the bypass valve at the gas outlet, the ventilation plate is arranged in the first annular groove, the check valve body is arranged adjacent to the outer side face of the ventilation plate and fixed to the valve body of the bypass valve by a screw, a sealing ring is arranged in a connection joint between the ventilation plate and the valve body of the bypass valve, and a sealing ring is arranged in a connection joint between the check valve body and the valve body of the bypass valve.

2. The bypass valve of claim 1, wherein, a third annular groove in communication with the first gas passage is arranged at an end of the check valve body that is connected with the ventilation plate;

the ventilation plate is substantially circular, a stepwise surface for mounting the sealing ring is arranged around the periphery of the ventilation plate, and the ventilation plate contains a center hole and a plurality of ventilation hole;

the first sealing gasket is arranged between the ventilation plate and the check valve body, and the gas outlet and the first gas passage are selectively communicated with each other by a movement of the first sealing gasket.

3. The bypass valve of claim 2, wherein, the first sealing gasket includes a disc and a rod arranged at the center of the disc, the first sealing gasket is arranged between the ventilation plate and the check valve body, the rod is extended through the center hole, the length of the rod is greater than the thickness of the ventilation plate, and a limit cap is arranged at a free end of the rod to prevent the first sealing gasket from releasing from the ventilation plate; when the disc is attached to the ventilation plate, the communication between the ventilation hole and the third annular groove is blocked, and hence the communication between the gas outlet and the first gas passage is blocked.

4. The bypass valve of claim 3, wherein, the outer diameter of the disc is smaller than the inner diameter of the third annular groove, a plurality of limit projections are arranged within the third annular groove, which is in communication with the first gas passage, and a pipe joint for exhausting gas is threadedly connected to the outer end of the first gas passage.

5. A bypass valve, comprising a valve body with a gas inlet and a gas outlet, wherein, a check valve including a check valve body, a ventilation plate and a first sealing gasket is arranged at the gas outlet, a first gas passage for gas delivering is arranged within the check valve body, the ventilation plate contains a ventilation hole in communication with the gas outlet, the first sealing gasket is arranged between the ventilation plate and the check valve body, and the first gas passage is selectively communicated with the ventilation hole by the first sealing gasket, wherein, a valve cover containing a second gas passage is arranged on the valve body of the bypass valve, the valve body of the bypass valve contains a third gas passage, a first cavity in communication with the gas inlet and a second cavity in communication with the first cavity, and the second cavity and the third gas passage are used for gas delivering when the bypass valve is not communicated with an evaporator, wherein, inner threads are arranged in an upper part of the first cavity, and the valve cover is provided with external threads matching with the inner threads, such that the valve cover is threadedly connected to the valve body; two grooves are circumferentially arranged on the valve cover at an upper side and a lower side of the external threads, respectively and each are used for accommodating sealing rings; where one of the sealing rings is located at the upper side of the external threads, while the other one of the sealing rings is located at the lower side of the external threads is used for enhancing the gas tightness between the valve cover and the valve body of the bypass valve;

the third gas passage is arranged under the first cavity and connected with the bottom of the first cavity, such that the second gas passage and the third gas passage are opposite to each other; a first boss corresponding to an outlet of the second gas passage is arranged at the bottom of the valve cover, and a second boss corresponding to an inlet of the third gas passage is arranged at the bottom of the first cavity.

6. The bypass valve of claim 5, wherein, a valve core is arranged in an assembly space formed by the second gas passage, the first cavity and the third gas passage, a second sealing gasket is arranged on the valve core and located between the first boss and the second boss, and the first cavity is selectively communicated with the second gas passage or the third gas passage by an up-and-down movement of the second sealing gasket.

7. The bypass valve of claim 6, wherein, the valve core includes a gland, an upper spring, a valve stem and a lower spring, which are sequentially connected from top to bottom;

a first projection is arranged at the upper portion of the gland, a second projection corresponding to the first projection is inwardly arranged at the top of the valve cover and located at an inlet of the second gas passage, the gland is limited within the second gas passage by the engagement between the first projection and the second projection, the gland is substantially cylindrical, four flat faces are formed evenly and longitudinally at the periphery of the gland, and guide portions with an arc-shaped cross section are arranged between the flat faces.

8. The bypass valve of claim 7, wherein, an upper installation groove is extended upwardly and inwardly from the bottom of the gland at the center of the gland and is chamfered at its opening, a lower installation groove is extended downwardly and inwardly from the top of the valve stem at the center of the valve stem, one end of the upper spring is arranged in the upper installation groove, while the other end of the upper spring is arranged in the lower installation groove;

an annular body is arranged in the middle of the valve stem, the upper surface of the annular body is tapered, an installation groove for the second sealing gasket is arranged on the valve stem immediately following the lower surface of the annular body, the second sealing gasket is arranged on the valve stem through the installation groove for the second sealing gasket, and a lower part of the valve stem extends through the lower spring, one end of which is arranged in the third gas passage and the other end of which is contacted with the lower surface of the second sealing gasket.

\* \* \* \* \*